United States Patent [19]

Court

[11] Patent Number: 4,852,728
[45] Date of Patent: Aug. 1, 1989

[54] ORAL HYGIENE DEVICE

[76] Inventor: John R. Court, 2631 Fordyce Rd., Ojai, Calif. 93023

[21] Appl. No.: 219,289

[22] Filed: Jul. 14, 1988

[51] Int. Cl.⁴ .............................................. A61B 19/02
[52] U.S. Cl. ................................................... 206/63.5
[58] Field of Search ............................. 206/63.3, 63.5

[56] References Cited

U.S. PATENT DOCUMENTS 3,608,566  9/1971  Storandt ..................... 206/63.5 X
4,579,221  4/1986  Corella ....................... 206/63.5 X
4,693,365  9/1987  Corella ....................... 206/63.5 X

FOREIGN PATENT DOCUMENTS 739347  10/1955  United Kingdom ............... 206/63.3

Primary Examiner—William Price
Attorney, Agent, or Firm—Freilich, Hornbaker, Rosen & Fernandez

[57] ABSTRACT

A disposable single use package comprised of a short length of dental floss integrated in a sanitary packet. The packet is formed by first and second members releasably attached to one another to form a sanitary interior compartment for accommodating the length of dental floss.

6 Claims, 2 Drawing Sheets 4,852,728

ORAL HYGIENE DEVICE

FIELD OF THE INVENTION

This invention relates generally to oral hygiene devices and more particularly to a disposable single use device comprised of a short length of dental floss integrated in a sanitary packet which can be readily opened for use.

BACKGROUND OF THE INVENTION

Toothpicks and dental floss are frequently used by persons to clean between their teeth.

It is well known to individually package toothpicks in inexpensive sanitary paper packets. Such packages are frequently made available by restaurants to their patrons for convenient single use application after which the toothpick and packet can be readily disposed of.

Dental floss, on the other hand, is typically packaged in long lengths on a spool. In use, a short length is severed from the spool for single use application with the package and remaining supply on the spool being retained for later use.

SUMMARY OF THE INVENTION

The present invention is directed to a disposable single use package comprised of a short length of dental floss whose first and second ends are respectively secured to first and second releasably attached members which together form a sanitary packet.

In accordance with the invention, the packet members are releasably attached to one another so as to form a substantially sealed interior compartment. A short length (e.g. eight inches) of dental floss is accommodated within the compartment with the first and second ends of the floss respectively secured to the first and second packet members. When a user detaches the two members, the length of dental floss will then be available for use and the members can function as convenient handles.

In accordance with a first embodiment, the packet members comprise first and second leaves formed of planar flexible material such as paper or plastic. The leaves are releasably attached to one another in superimposed fashion, along a substantially peripheral seal line. The seal line can be formed in part by a fold line between leaves comprising portions of the same piece of material, by adhesive applied between the leaves, by crimping, or by other suitable means appropriate to the material. When the leaves are detached from one another, the user can then readily crumple or wad the leaves to facilitate their use as handles.

In accordance with a second embodiment, the packet members comprise first and second shells formed, for example, of plastic, which can be nested together in opposed fashion to form a capsule. The length of dental floss is accommodated in the capsule with the ends being respectively secured to the first and second shells.

In accordance with a third embodiment, the packet is formed by rolling a small sheet of flexible material, e.g. paper or plastic, into a substantially cylindrical roll structure. A reduced strength line, e.g. a perforated scoreline, is formed in the sheet to define first and second members which are thus releasably attached along the scoreline. Prior to rolling the sheet, the first and second ends of the dental floss are respectively secured to the first and second members. The roll structure can be broken along the scoreline to separate the members and enable the dental floss to be used with the members serving as end handles for the dental floss.

In accordance with a useful feature of the third embodiment, the sheet can be rolled diagonally or otherwise shaped to form substantially pointed ends on the roll structure. These pointed ends can be used as a conventional toothpick.

DETAILED DESCRIPTION

The present invention is directed to an inexpensive disposable package for making available to users an appropriate single use length of dental floss. Embodiments of the present invention have application in restaurants and other eating establishments for distribution to patrons, as has been a common practice with respect to toothpick packages. Additionally, however, embodiments of the invention would have application in private use, hospital use, etc.

Figure 1:
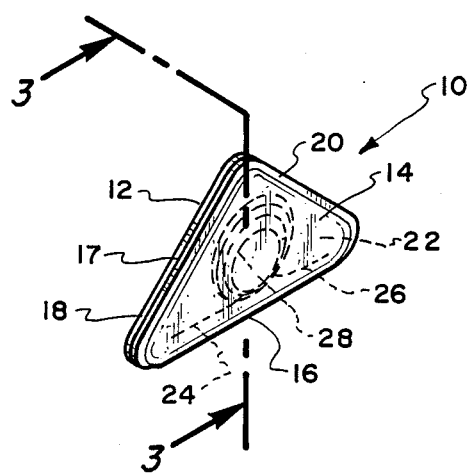
FIG. 1 is an isometric external view of a preferred embodiment of the invention.
Figure 3:
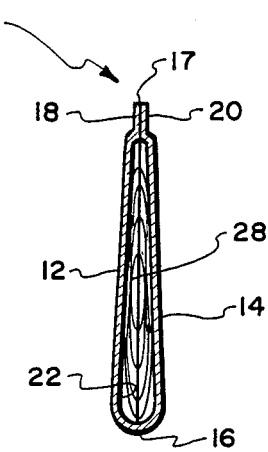
FIG. 3 is an enlarged sectional view taken substantially along the plane 3—3 of FIG. 1.
Figure 2:
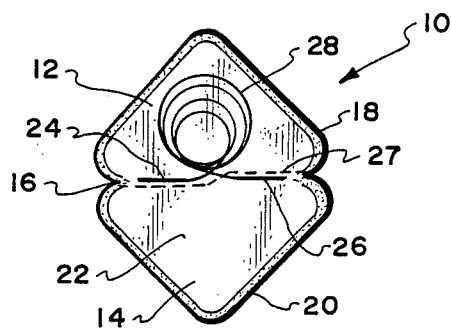
FIG. 2 is a plan view of a preferred embodiment of the invention showing the packet open with the two leaves joined along a common foldline.

FIGS. 1–3 depict a preferred embodiment of the invention comprising a substantially triangularly shaped packet 10. The packet 10 is formed of first and second triangularly shaped leaves 12 and 14 which are superimposed upon one another to form the packet 10. For convenience in manufacture, the leaves 12 and 14 can be formed of a single piece of material folded upon itself along a foldline 16 as shown in FIG. 2. The leaves 12 and 14 are preferably formed of flexible planar material, e.g. paper or a suitable plastic. Regardless of the material, in accordance with the invention, the leaves 12 and 14 are releasably attached together along a seal line 17 extending proximate to the peripheral edges 18 and 20 of the leaves and surrounding an interior space or compartment 22.

The seal line 17 forms a substantially continuous line around compartment 22 and is formed in part by the foldline 16. The remainder of the seal line 17 is formed by a suitable adhesive or by crimping the leaves 12 and 14 together. If plastic material is used, the seal line can be formed by the application of heat. In any event, it is intended that the leaves 12 and 14 be joined or sealed to one another along a substantially continuous line 17 so that the interior space or compartment 22 is maintained sanitary.

Prior to attaching the leaves 12 and 14, the first and second ends 24, 26 of a short coil (e.g. 8 inch length) of dental floss 28 are secured to the respective leaves. More specifically, as can be best seen in FIG. 2, end 24 is secured to leaf 12 and end 26 is secured to leaf 14. The securement can be by an appropriate adhesive or by a heat weld if the materials are properly selected. Note that with the ends 24 and 26 respectively secured to the leaves 12 and 14, the dental floss 28 can be retained within the sanitary compartment 22.

The means for attaching the leaves 12 and 14 to one another, whether it be by adhesive, crimping, heat welding, etc., should be readily releasable to permit a user to easily detach the leaves, as by moving the leaves relative to one another by rubbing the packet between the user's fingers. Releasable adhesives suitable for attaching the leaves together are readily available. In the embodiment of Figure 2, a reduced strength perforated scoreline 27 is formed proximate to the foldline 16, extending partially along leaf 12 and partially along leaf 14, to permit ready detachment. This permits the floss ends 24, 26 to be aligned so that they can be respectively attached to the leaves 12, 14 with a single straight line application of adhesive.

Figure 4:
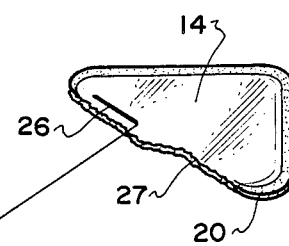
FIG. 4 is an isometric view showing the leaves separated with the dental floss ready for use.
Figure 4:
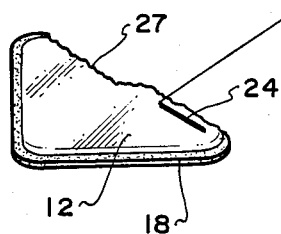

When the user detaches the leaves 12 and 14 from one another, he can then separate them to fully extend the length of dental floss 28, as depicted in FIG. 4. The dental floss will then be ready for use and the separated leaves 12 and 14 secured to the ends 24, 26 of the dental floss can be crumpled to readily serve as handles to facilitate use.

Figure 5:
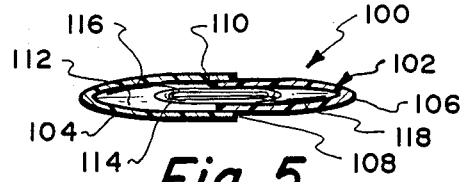
FIG. 5 is a plan view of a second embodiment of the invention in which the packet comprises a capsule formed by two opposed releasably attached shells.
Figure 6:
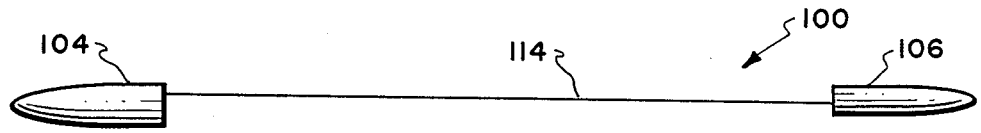
FIG. 6 depicts the embodiment of FIG. 5 showing the two plastic shells detached from one another.

Attention is now directed to FIG. 5 which illustrates a second embodiment 100 of the present invention including a packet 102 comprised of shells 104, 106, preferably formed of rigid or semi rigid plastic. The mouth 108 of shell 104 is dimensioned to be slightly larger than the outer dimension around mount 110 of shell 106. As a consequence, the shells can be nested in opposed relationship as shown in FIG. 5 to thus define an interior compartment 112. A length of dental floss 114 having first and second ends 116, 118, is accommodated within the compartment 112. End 116 is secured to the interior wall of shell 104 and end 118 is secured to the interior wall of shell 106.

The shells 104 and 106 are releasably detached either by being dimensioned sufficiently closely to be force fit or by an application of a suitable adhesive around the adjacent surfaces of the outer wall of shell 106 and/or the inner wall of shell 104. Being so attached, a user can readily separate the two shells, as by twisting them relative to one another, to thereby make the dental floss length 114 available for use with the separated shells 104 and 106 functioning as rudimentary handles.

Figure 7:
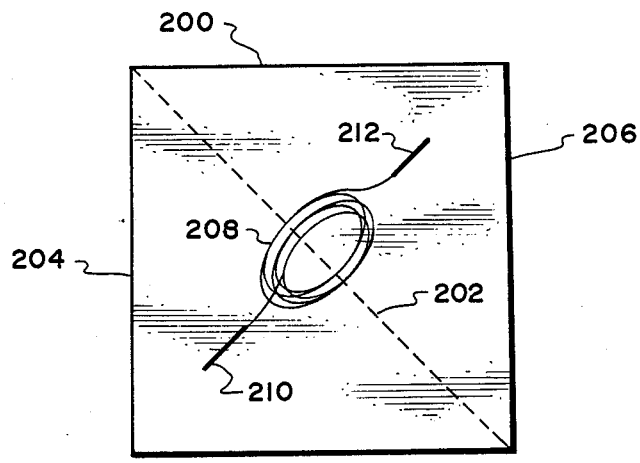
FIG. 7 depicts a third embodiment of the invention comprising a single piece of flat material which can be rolled to form a substantially cylindrical roll structure.
Figure 8:
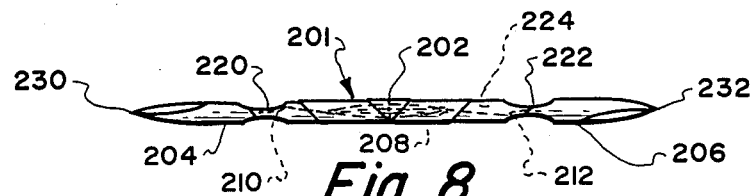
FIG. 8 is a plan view depicting the roll structure resulting from rolling the piece of material shown in Figure 7.
Figure 9:
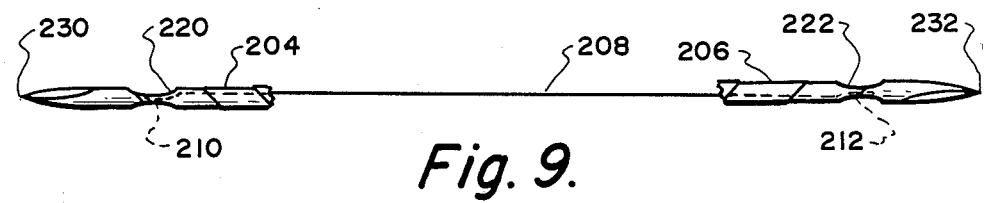
FIG. 9 depicts the embodiment of FIG. 8 showing the two packet members, i.e. two halves of the roll structure of FIG. 8, detached.

Attention is now directed to FIGS. 7-9 which illustrate a third embodiment of the present invention. the embodiment of FIG. 8 is formed by rolling a single sheet 200 into a substantially cylindrical structure 201. More specifically, FIG. 7 illustates a substantially rectangular sheet of flat flexible material, e.g. paper or plastic. A reduced strength scoreline 202 is formed in the sheet 200 thus partitioning the material into members 204 and 206. Prior to rolling the sheet 200 to form the roll structure depicted in FIG. 8, a length of dental floss 208 is secured to the sheet by attaching end 210 to member 204 and end 212 to member 206. Thereafter, the sheet 200 can be rolled to form the substantially cylindrical roll structure 201 depicted in FIG. 8. By crimping the roll structure near its ends, e.g. at 220, 222, a sealed interior compartment 224 is created which accommodates the length of dental floss 208.

A user can break the roll structure 201 along the scoreline 202 to thus separate the members 204 and 206 to make the dental floss 208 available for use. The members 204 and 206 will then serve as handles to facilitate the use and handling of the floss 208.

The utility of the roll structure 201 of FIG. 8 is enhanced by rolling the sheet 200 to form pointed ends 230, 232. If the sheet of material 200 is formed of sufficiently heavy stock, then the roll structure 201 will have intermediate utility as a toothpick with the user using the pointy ends 230 and 232. After the roll structure 201 has been used in a conventional manner as a toothpick, it can then be broken apart as represented in FIG. 9 to make the dental floss 208 available for use.

From the foregoing, it should be understood that a disposable single use package has been disclosed herein comprised of a sanitary packet and a length of dental floss retained in a compartment formed in the packet. Although particular embodiments of the invention have been disclosed, it should be readily recognized that many structural variations are available, and accordingly, it is intended that the appended claims be interpreted to include such variations.

What is claimed is:

1. A dental floss package comprising:
   a single use length of dental floss having first and second ends;
   a packet comprised of first and second members;
   means respectively attaching said first and second ends to said first and second members; and
   means releasably attaching said first and second members to one another so as to form an enclosed interior compartment for accommodating said length of dental floss;

2. The package of claim 1 wherein said substantially cylindrical structure is shaped to define at least one pointed end to facilitate use of said structure as a toothpick.

3. An oral hygiene device comprising:
   first and second flexible planar members;
   releasable attaching means adhering opposing surfaces of said first and second members in superimposed relationship along a peripheral seal line to define a substantially sealed interior compartment between said members;
   a single use length of dental floss having first and second ends;
   said dental floss being accommodated in said compartment with said first end secured to said first member and said second end secured to said second member whereby release of said members from one another yields said length of dental floss with each end thereof having a planar member secured thereto.

4. The device of claim 3, wherein said first and second members comprise portions of a planar sheet folded upon itself along a foldline; and
   a reduced strength scoreline formed in said sheet proximate to said foldline, to partition said sheet into said first and second members.

5. The device of claim 4 wherein said scoreline includes a first portion extending along said sheet to one side of said foldline and a second portion extending along said sheet to the other side of said foldline; and wherein said floss first and second ends are respectively secured to said first and second members in alignment substantially along said foldline whereby detachment of said members along said scoreline yields said first member attached to said first end and said second member attached to said second end.

6. The device of claim 5 wherein said scoreline includes a third portion connecting said first and second portions.

* * * * *